(12) United States Patent
Whipple et al.

(10) Patent No.: US 9,999,457 B2
(45) Date of Patent: *Jun. 19, 2018

(54) ORTHOPEDIC FASTENER (71) Applicant: Amendia, Inc., Marietta, GA (US)

(72) Inventors: Dale Whipple, Acworth, GA (US);
Kenneth Richard Barra, Acworth, GA (US)

(73) Assignee: Amendia, Inc., Marietta, GA (US)

( * ) Notice: Subject to any disclaimer, the term of this patent is extended or adjusted under 35 U.S.C. 154(b) by 229 days.

This patent is subject to a terminal disclaimer.

(21) Appl. No.: 14/863,631

(22) Filed: Sep. 24, 2015

(65) Prior Publication Data
US 2016/0008047 A1 Jan. 14, 2016

Related U.S. Application Data

(60) Division of application No. 14/551,659, filed on Nov. 24, 2014, now Pat. No. 9,179,955, which is a continuation-in-part of application No. 14/156,782, filed on Jan. 16, 2014, now Pat. No. 9,463,057, and a continuation-in-part of application No. 14/538,860, filed on Nov. 12, 2014, now Pat. No. 9,055,986.

(51) Int. Cl.
*A61B 17/86* (2006.01)
*A61B 17/70* (2006.01)
*F16B 35/04* (2006.01)
*F16B 25/00* (2006.01)

(52) U.S. Cl.
CPC ........ *A61B 17/8625* (2013.01); *A61B 17/863* (2013.01); *A61B 17/8635* (2013.01); *A61B 17/7037* (2013.01); *A61B 17/8605* (2013.01); *F16B 25/0052* (2013.01); *F16B 25/0057* (2013.01); *F16B 35/04* (2013.01)

(58) Field of Classification Search
CPC ............... A61B 17/8625; A61B 17/863; F16B 25/0052; F16B 25/0057
See application file for complete search history.

(56) References Cited

U.S. PATENT DOCUMENTS 2,382,019 A 8/1945 August
5,259,398 A * 11/1993 Vrespa ................. A61B 17/863
128/898

(Continued)

FOREIGN PATENT DOCUMENTS

WO 2013068088 5/2013

*Primary Examiner* — Nicholas Woodall
(74) *Attorney, Agent, or Firm* — David L. King (57) ABSTRACT

An orthopedic fastener has a head and a shank. The shank has a leading end portion adjacent a distal tip and a trailing end portion adjacent a head. An intermediate portion is positioned between the leading and trailing end portions. At the intermediate portion, the shank increases in diameter. The leading end portion has a first thread which includes one or more self-tapping cutting grooves extending adjacent the distal tip and through a plurality of the first threads. The intermediate portion has second threads extending toward the head from the leading end portion. The second threads of the intermediate portion are larger in outer diameter than the first threads in the leading end portion. The intermediate portion has one or more cutting grooves traversing at each of a leading transition at the leading end portion and at a trailing transition.

12 Claims, 6 Drawing Sheets

(56) References Cited

U.S. PATENT DOCUMENTS

| | | | |
|---|---|---|---|
| 5,593,410 A | 1/1997 | Vrespa | |
| 5,601,553 A | 2/1997 | Trebing | |
| 6,030,162 A | 2/2000 | Huebner | |
| 6,565,573 B1 | 5/2003 | Ferrante | |
| 8,075,604 B2 | 12/2011 | Denis et al. | |
| 8,333,590 B2 | 12/2012 | Hansson | |
| 8,419,779 B2 | 4/2013 | Rinner | |
| 8,511,958 B2 * | 8/2013 | Chang | F16B 25/103 411/387.1 |
| 8,740,955 B2 * | 6/2014 | Bottlang | A61B 17/8042 606/286 |
| 2012/0178048 A1 | 7/2012 | Cottrell | |
| 2013/0218213 A1 | 8/2013 | Lemoine | |
| 2014/0012334 A1 * | 1/2014 | Armstrong | A61B 17/863 606/309 |
| 2014/0142636 A1 | 5/2014 | Hes | |

\* cited by examiner

FIG. 12

ORTHOPEDIC FASTENER

RELATED APPLICATIONS

This application is a division of U.S. application Ser. No. 14/551,659 filed Nov. 24, 2014 entitled "Improved Orthopedic Fastener" which is a continuation in part of U.S. Ser. No. 14/538,860 filed Nov. 12, 2014, now U.S. Pat. No. 9,055,986 issued Jun. 16, 2015, entitled "Improved Orthopedic Fastener" which is a continuation in part of U.S. Ser. No. 14/156,782 filed Jan. 16, 2014 entitled "Improved Orthopedic Fastener".

TECHNICAL FIELD

The present invention relates generally to bone fasteners, more particularly to an improved orthopedic fastener with an improved thread cutting feature to secure the fastener in bone

BACKGROUND OF THE INVENTION

In orthopedic bone repair procedures, a variety of devices and implants have been devised to stabilize a bone fracture or to space vertebrae or attach ligaments or tendons to bone. Most of these devices require the use of threaded fasteners or screws that are driven into the bone and held or anchored in place to the bone.

The bone structure typically has a hard outer surface or shell commonly referred to as cortical bone and a softer interior of a more open celled spongy structure of cancellous bone. Accordingly, the fastener must be held in place taking into account the structure of the bone.

A variety of unique thread configurations for bone screws have been developed for this purpose, the goal being to provide a safe and reliable fastening into the bone material.

The present invention provides a unique and advantageous design to create secure attachment of a bone fastener. Loosening of the fastener and damaging the threads cut into the bone are primary limitations of prior art fasteners.

These and other limitations in the prior art have been corrected and solved by the present invention as disclosed herein.

SUMMARY OF THE INVENTION

An orthopedic fastener has a head and a shank. The shank extends from the head to a distal tip. The shank has a leading end portion adjacent the distal tip and a trailing end portion adjacent the head. An intermediate transition is positioned between the leading and trailing end portions. At the intermediate transition, the shank increases in diameter. The leading end portion has a first thread which optionally may include one or more self-tapping cutting grooves extending adjacent the distal tip and through a plurality of the first threads. The trailing end portion has second threads extending toward the head from the intermediate transition. The second threads of the trailing end portion are larger in outer diameter than the first threads in the leading end portion. The intermediate transition has one or more cutting grooves traversing the increasing diameter. Preferably, the intermediate transition has the one or more second cutting groove extending from at least a first thread in the intermediate transition through at least one of said second threads to initiate tapping of the larger diameter threads of the trailing end portion into cortical bone. The optional first cutting grooves, if used, and the one or more cutting grooves in the intermediate transition, in combination with the threads form threads in the bone to hold the fastener, the first threads being positioned in cancellous bone and the second threads in harder cortical bone on insertion.

The first thread can have a pitch equal to said second thread. In one embodiment, the first thread has a pitch equal that of the larger diameter second thread and the first thread extends between the distal end portion increasing in diameter at the intermediate transition to equal the diameter of the second threads toward the head through the trailing end portion and the second thread extends helically spiraled between the first threads.

The orthopedic fastener wherein the self-tapping one or more cutting grooves allow for the combination of the first and second threads in the trailing end portion to cut increasing the diameter of first threads previously formed in the bone and creating the larger cut second formed threads without damaging the bone threads and wherein a recess may be positioned between the head and the end of the threads in the trailing end portion. The orthopedic fastener can be an implantable metal. The implantable metal can be one of titanium, stainless steel or cobalt chrome.

BRIEF DESCRIPTION OF THE DRAWINGS

The invention will be described by way of example and with reference to the accompanying drawings in which.

DETAILED DESCRIPTION OF THE INVENTION

Generally, an orthopedic fastener of this invention includes a head and a shank extending from the screw head to a distal tip. As used herein the term "head" means any head or top end of a fastener. The screw shank has trailing end portion including a recess adjacent to the head of the fastener, an intermediate transition section, and a leading end portion adjacent to the distal tip. In at least one embodiment, the fastener also includes a substantially continuous thread along at least a portion of the shank which extends radially outward from the shank.

The fastener of this invention is adapted to be used alone or in conjunction with a system for use in repairing a bone fracture or in fixing an orthopedic implant in a patient. The fastener can be used alone to aid in the reduction of small bone fractures. Additionally, a fastener according to this invention can be used in conjunction with an orthopedic implant to fix the implant securely to the skeletal system of the patient.

FIGS. 1 through 5 depict one embodiment of a fastener 10 according to this invention. As shown in the figures, orthopedic fastener 10 includes a head 50 and a shank 20. Preferably, head 50 is adapted to contact the bone. The shank 20 extends from head 50 to a distal tip 11. A continuously extending first thread 40 extends evenly about the outer surface of the shank 20. The leading end portion adjacent distal tip 11 includes a fluted groove 41 for the removal of bone chips as the fastener 10 is implanted into the bone. Tip 11 of the fastener 10 is a self-tapping, non-self-drilling tip with a generally conical configuration with a foreshortened end, e.g. a frusto-conical tip.

Preferably, fastener 10 is a self-tapping, non-self-drilling bone screw so that tip 11 requires a predrilled hole before insertion into the bone and only first threads 40 of fastener 10 initially cut into the bone. The pitch of the threads 40 at tip 11 should be sufficiently small to advance the fastener 10 at a rate which allows tip 11 to advance into the bone, but sufficiently large to provide adequate bone purchase and to minimize the number of turns required to seat the fastener 10. A suitable pitch for threads 40 may be in the range of about 5 threads-per-inch to about 50 threads-per-inch.

In the preferred embodiment, the first threads 40 use a double start 40A, 40B thread with a high helix angle. Each is shown 180 degrees at the distal tip 11. At the trailing end portion 3 and the intermediate transition 2, the second threads 60 are also a double or two start thread 60A, 60B. This combination at the intermediate transition 2 initiates the additional two starts so the fastener 10 has four starts 40A, 40B and 60A, 60B as illustrated.

Each thread start preferably has one cutting groove. These cutting grooves are positioned at the beginning of each thread start. Accordingly, when there are two starts there are two cutting grooves spaced 180 degrees apart. This is as shown in the exemplary embodiment. Had three thread starts been employed, there would be three cutting grooves. In the present invention, the second set of threads has two starts so the fastener 10 has four cutting grooves, a first pair at the distal end and a second pair at the intermediate transition. In the illustrated embodiments, the second pair of cutting grooves are shown aligned with the first pair. This is a simple design preference since the two second thread starts could be at any location, the second pair of cutting grooves could be at any angle or location relative to the first pair. The important thing is each thread start within a pair in the present invention is 180 degrees apart. So the cutting grooves are 180 degrees apart in the transition 2 and similarly 180 degrees in the leading end portion 1 and, as shown, the intermediate grooves are aligned with the leading grooves along the shank. Alternatively, the starts and grooves relative to another section or end could be positioned at any angle relative to the other end or section. This is possible due to the second threads being started in a spaced location removed from the leading end portion 1 and distal tip 11 in the intermediate transition section 2.

The length of the fastener 10 should be adapted to correspond to the use. The fastener 10 can be any suitable length; preferably, the length of the fastener 10 is generally from about 20 mm to about 160 mm. More preferably, the length of fastener 10 is from about 30 mm to about 65 mm; preferably, the length of the shank 20 is approximately 4 to 6 mm less than the total length of the fastener, depending on the head shape and length.

Figure 1:
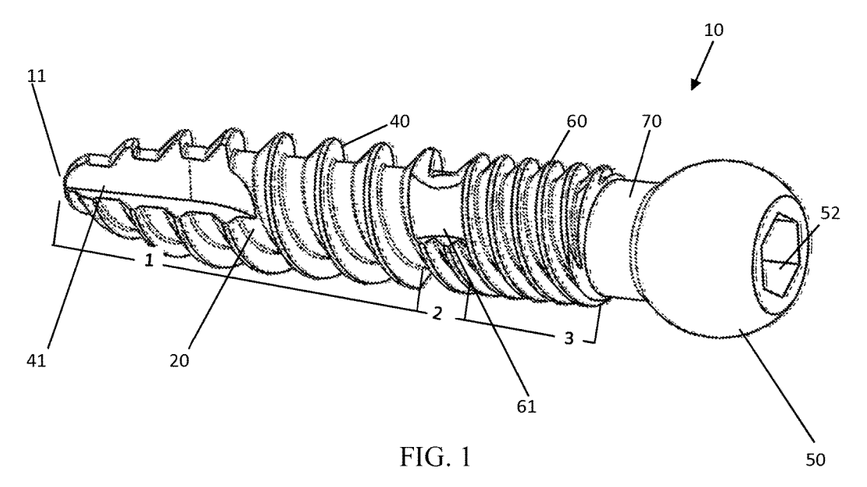
FIG. 1 is a perspective view of a bone screw or orthopedic fastener according to one embodiment of this invention.
Figure 2:
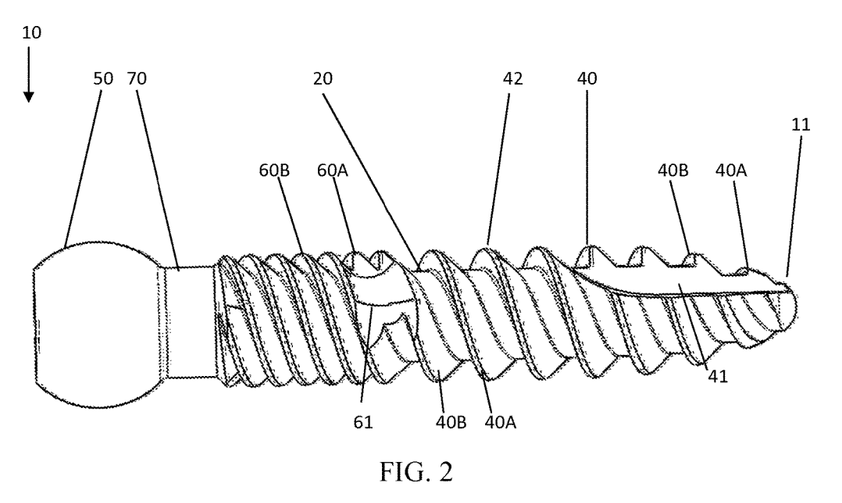
FIG. 2 is a side view of the fastener of FIG. 1.
Figure 3:
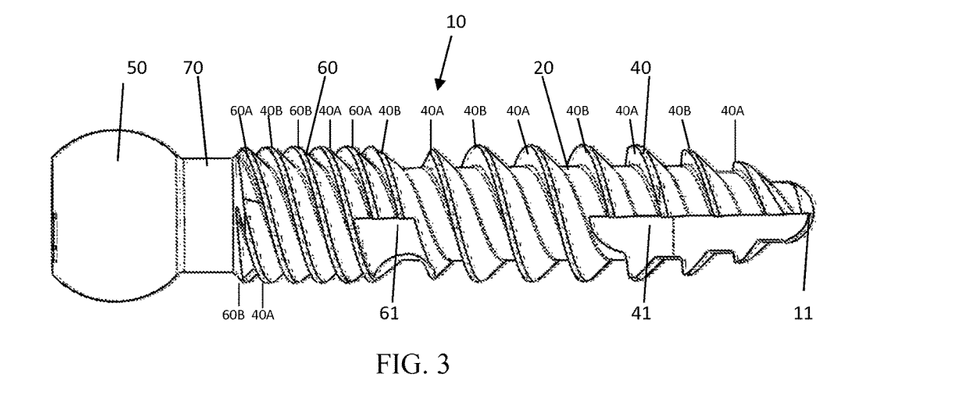
FIG. 3 is a top plan view of the fastener of FIG. 1.
Figure 4:
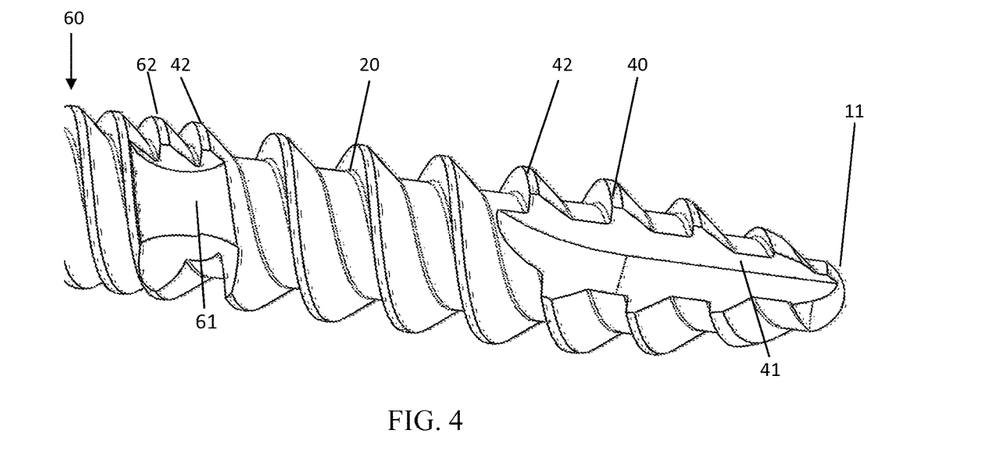
FIG. 4 is a partial perspective view of the fastener of FIG. 1.
Figure 5:
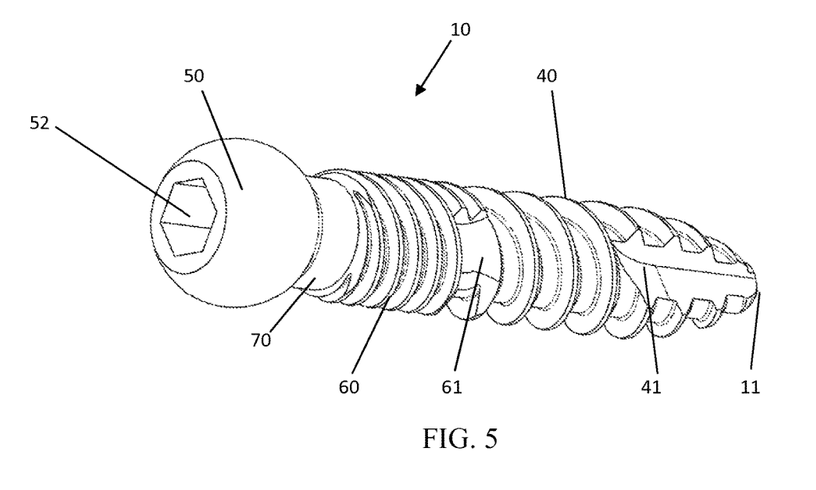
FIG. 5 is a perspective view of the head and internal surface of the fastener head of the fastener.

FIG. 4 is a side view of the fastener 10 of FIG. 1 and shows the detailed characteristics of the shank 20 and thread 40 of fastener 10. Shank 20 has a minor diameter and the first thread 40 a major diameter 42, defined by the diameter of the first thread 40. The thread height is equal to one half of the difference between the minor diameter and the major diameter 42. The difference is divided by two to account for the thread height on either side of the shank 20. Alternatively, the major diameter can be described as the sum of the minor shank diameter and twice the thread height. Note that shank minor diameter and thread major diameter and thread height can vary along the length of the fastener, as described below.

Shank 20 has three sections: trailing end portion 3; intermediate transition or section 2; and leading end portion 1. Trailing end portion 3 is the portion of the shank 20 adjacent to head 50, leading end portion 1 is the portion of the shank 20 adjacent to the frusto-conical distal tip 11, and intermediate section 2 is the portion of the shank 20 between the leading and trailing end portions. Each shank section has a minor shank diameter which may or may not remain constant from one section to another or within a section itself Thus, trailing end portion has a first minor diameter, intermediate section as a second minor diameter, and leading end portion has a third minor diameter.

Intermediate section 2, of the embodiment shown in FIGS. 1-6, has a generally cylindrical geometry with a substantially constant minor diameter. The minor diameter can be any suitable length adapted to the size and function of the fastener. Preferably, the second minor diameter of the fastener 10 of the present invention is generally from about 6.0 mm to about 3.5 mm, more preferably from about 5.5 mm to about 4.0 mm, and most preferably from about 5.0 mm to about 4.5 mm.

In the embodiment shown, leading end portion 1 includes a taper or curvature extending from the end of the intermediate section 2 to the tip 11 at an angle theta θ or radius of curvature. Theta θ angle may also be any suitable angle, and is generally from about 1 degree to about 8 degrees, and preferably from about 1 degree to about 3 degrees. Thus, leading end portion 1 has a generally tapered geometry such that the minor diameter decreases from the section adjacent to intermediate section 2 in the direction of tip 11. The taper narrows towards the tip of the fastener 10 creating a frusto-conical tip area. The curvature has a radius or multiple radii to form a narrowing bullet like shape. This narrowing shape at the tip 11 end allows the fastener 10 to follow the pre-drilled hole more effectively and to advance more easily into the bone and through an aperture in an orthopedic implant.

Additionally, the first thread 40, thread height, and major diameter of a fastener 10 of this invention may vary along the length of the fastener body. As with the minor diameter, each shank section 1, 2 or 3 has a corresponding thread section and major diameter defined by the relative thread height.

First threads 40 extend in intermediate section 2 and have a substantially constant thread height due to the substantially constant second minor diameter of shank 20 and second major diameter in intermediate section 2. The major diameter of the thread is suited to the size of the fastener 10 and the intended function; preferably, the major diameter is from about 4.5 mm to about 8.5 mm, more preferably from about 5.5 mm to about 7.5 mm. Additionally, the ridge top of intermediate thread section can be relatively broad and wide as if the pointed end has been shaved off This flat ridge top can be useful in the soft trabecular region of the bone where the leading end portion 1 and the intermediate section 2 will reside. The flat ridge top and constant minor diameter of the intermediate section also suit a fastener adapted for insertion through an aperture in an orthopedic implant for fixing the implant to the skeletal system of a patient.

Taper on leading end portion 1 results in a decreasing minor diameter, but the third major thread diameter is the same as second major thread diameter in the intermediate section 2 and trailing section 3. The substantially constant major diameter through intermediate section 2 and trailing end portion 3 results in a thread height of the threads along leading end portion 1 that is greater than the thread height of threads in intermediate section 2 and the trailing end portion 3. This increased thread height provides a better "bite" or grasp into the bone and more effectively draws the fastener 10 into the bone. The ridge top in this leading end portion 1 can be narrow, or pointy, for better pull through and purchase, particularly on the far cortex of the bone. The cortex, unlike the trabecula, is hard and provides strength to the bone, and thus requires a stronger grasp.

In trailing end portion 3 the thread heights 42, 62 of first and second threads 40, 60 are the same or slightly less than thread height 42 of the first threads 40 in the intermediate transition section 2 because both the minor shank diameter and the major thread diameter increase or stay the same along no taper or a slight taper in the direction of the head 50. A space is left between the threads and the head 50 providing room for a recess 70. This recess 70 can have an enlarged shank diameter for increased strength, and a tight wedge fit of the trailing end portion 3 of the fastener 10. The ridge top of threads 40, 60 along trailing end portion 3 is also generally narrow and pointy to provide for better seating of the fastener 10 and better purchase in the hard bone material of the near cortex.

The dual tapers, and an increased height of threads 40, 60 on the intermediate section 2 and trailing end portion 3 of fastener 10 provides improved purchase on both the near and far cortex of the bone. Intermediate section 2 with its second cutting groove 61 does not require a tapered geometry or a high thread height because it can lie in and occupy the inner portion of the bone with trabecular bone tissue, a softer, spongy bone tissue, and optionally occupies the interior of an aperture in an orthopedic implant when the fastener is used for fixing an orthopedic implant in a patient.

As discussed above, the trailing end portion 3 of shank 20 has an enlarged minor diameter to provide structural reinforcement for the recess 70 adjacent the head 50. In one embodiment of the invention, the head 50 includes a geometrically shaped socket 52 adapted to engage a corresponding driver and an axial bore extending from the bottom of the socket 52 into the upper portion of the fastener shank 20. The bore can include a connecting structure that corresponds to connecting structure on the driver. The connecting structure may be any suitable structure that couples the fastener to the driver, such as threads, or a snap ring. The orthopedic fastener can be an implantable metal. The implantable metal can be one of titanium, stainless steel or cobalt chrome.

Figure 6:
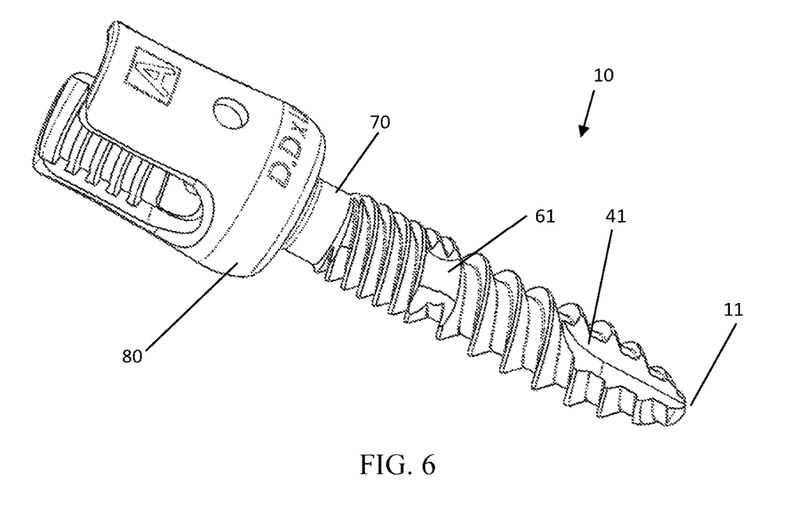
FIG. 6 is a view of the fastener of the present invention with a tulip attached.

As shown in FIG. 6, the fastener 10 can be used with a tulip 80.

Figure 7:
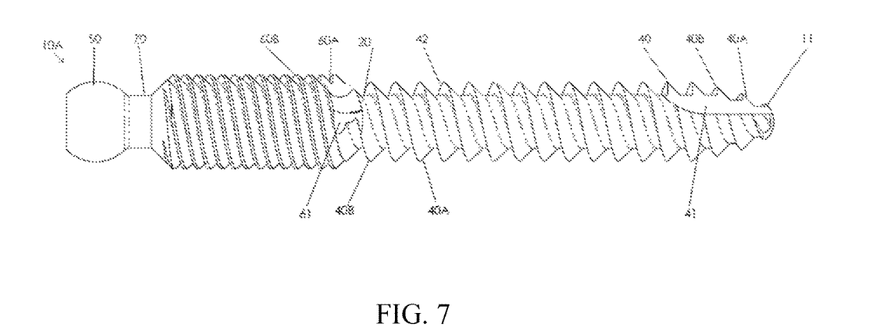
FIG. 7 is a side view of the bone screw or orthopedic fastener of a second embodiment having a stepped up dual diameter configuration.
Figure 8:
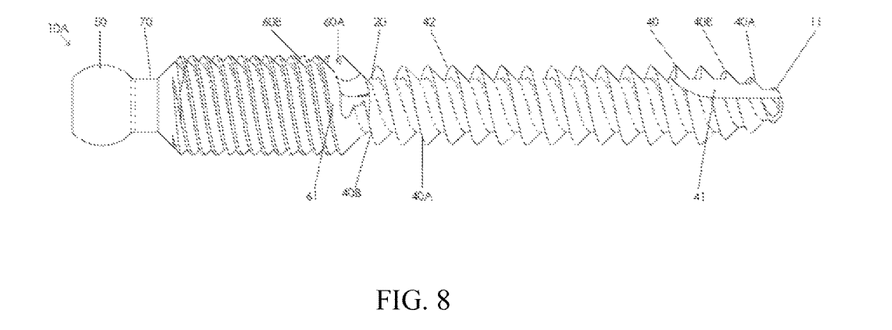
FIG. 8 is a side view of a different sized second embodiment of the present invention.

With reference to FIGS. 7 and 8, orthopedic fastener 10A is illustrated. Fastener 10A has all the features of fastener 10 and those common elements are marked accordingly with the same reference numerals. A key distinction of the fastener 10A is the trailing end portion 3 second threads 60 have a stepped up larger outer diameter. This increased diameter initiates in an intermediate section or transition region 2. The shank 20 increases in diameter, preferably rather smoothly in a conical fashion as the first threads 40 in this region 2 similarly increase in outer diameter. As shown, the fastener 10A has cutting grooves 61 in this stepped up diameter intermediate section transition region 2. These cutting grooves 61 allow the fastener 10A to either enlarge the bone formed threads created by the first threads 40 on entry or can cut these bone threads away to accommodate the larger threads 60 in the trailing portion 3.

As previously discussed, the first thread 40 can be helically intertwined with the second thread 60, but in this second embodiment, the fastener 10A has the first thread 40 increase in outer diameter through the transition region 2 to the same enlarged diameter of the second thread 60. As with the first embodiment, the trailing end portion 3 threads 60 are ideal for fastening into the hard cortical bone while the leading end portion 1 threads 40 will fasten into the softer cancellous bone.

Optionally, the leading end portion 1 adjacent the tip 11 can also have cutting grooves 41. In some cases, a surgeon may want to pre-drill the bone making initial entry self-tapping first thread 40 optional or unnecessary; however, on fastening to bone, the cutting grooves 61 in the intermediate transition region 2 enlarges the bone thread to accommodate the larger second threads 60 and can be fashioned to insure a very tight fit without fracturing the cortical bone. This insures the bone fastener 10A fits more securely to the bone without damaging the underling bone first threads in the cancellous bone region. This increase in thread diameters preferably is kept within 1 to 2.0 mm, a 1 mm thread increase in small sizes like 6.5 mm to 7.5 mm and a larger increase in size from the 8 5 mm to 10 mm are easily accommodated. The overall length of the screws is typically 20 mm to 40 mm with the trailing threads being less than half the total length, typically 30 percent to about 25 percent of the total threaded length. This reflects the bone structure having a rather thin depth in the hard cortical bone compared to the softer cancellous bone into which the fastener 10A is attached. It is understood the sizes and dimensions can be varied to reflect specific orthopedic applications.

Figure 9:
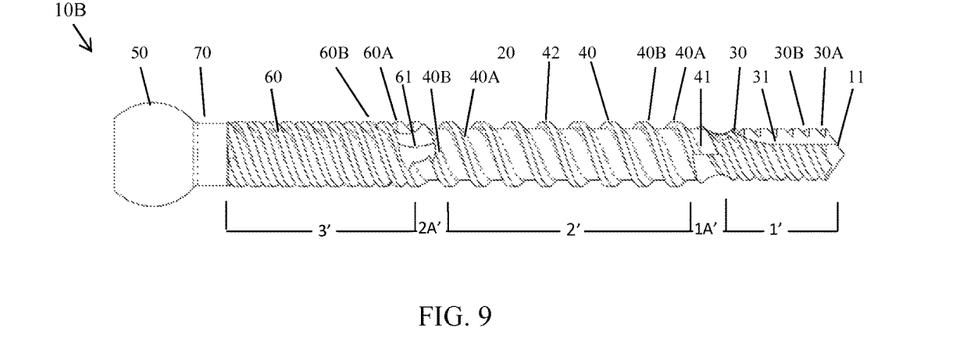
FIG. 9 is a side view of a third embodiment of the present invention.
Figure 10:
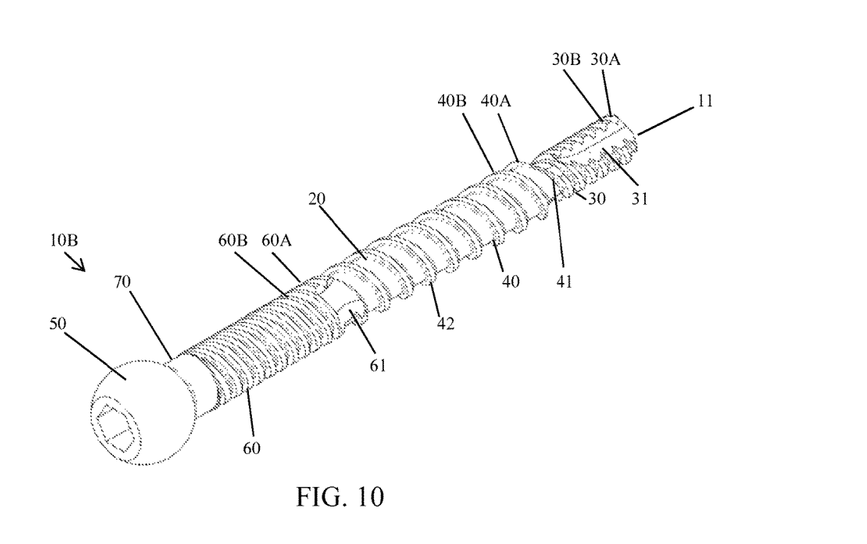
FIG. 10 is a perspective view of the third embodiment of FIG. 9.

With reference to FIGS. 9 and 10, a third embodiment of the present invention is illustrated. This third embodiment 10B is an orthopedic fastener having a head 50 and a shank 20; the shank 20 extends from the head 50 to a distal tip 11. The shank 20 has a leading end portion 1' adjacent the distal tip 11, a trailing end portion 3' adjacent the head 50 and an intermediate portion 2' positioned between the leading 1' and trailing end 3' portions. As shown, the intermediate portion 2' has a pair of transitions, a first leading transition 1A' at the leading end portion 1' and a second trailing transition 2A' at the trailing end portion 3'. As shown, the intermediate portion 2' increases in diameter to a slightly larger diameter relative to the leading end portion 1'. As shown, the leading end portion 1' has threads 30 and cutting grooves 31 adjacent the tip 11. At the first leading transition 1A', additional cutting grooves 41 are shown wherein a second set of threads 40 are illustrated. The second set of threads 40 are more widely spaced and are adapted to cut and be positioned, when fully inserted, into the cancellous bone material, whereas the leading end portion 1' has more tightly wound threads 30 adapted to cut and penetrate from the exterior surface or cortical bone, through the cortical bone. This self-tapping feature of the third embodiment facilitates entry of the screw into the bone by the reduction in size of the tip 11 and the threaded leading end portion 1'.

With further reference to the third embodiment screw 10B, it is noted that the trailing end at the intermediate trailing transition 2A' a second group of cutting threads 61 are positioned. These cutting grooves 61 transition to a third set of threads 60. The third set of threads 60 are more tightly wound helically about the shank 20, as illustrated. Furthermore, due to the construction of the threads, the threads 60 relative to the shank 20 have a shorter height from the shank to an outside diameter of the thread. These more tightly wound threads 60 are ideally adapted to cut into the cortical bone using the second threads 40, following that path and introducing additional threads into the cortical bone to match the profile of the third threads 60 in this trailing end portion 3'. As shown, in this embodiment, the second threads 40 for the cancellous bone are the same outer diameter as the third threads 60 in the trailing portion 3'. This greatly facilitates the entry of the screw into the bone.

As shown, the leading threads 30 are formed either as a double helix or quadruple helix wrapped about the shank 20. As the first threads 30 approach the intermediate portion 2' at the leading transition 1A', one or more of the thread helices terminates and one or more of the first threads 30 can continue through the intermediate portion, thereby forming the second threads 40. In doing so, it is necessary that the first threads 30 have a pitch similar to the pitch of the second threads 40 such that when one of the helix or helix pairs traverses the transition, it can increase in diameter maintaining the pitch so the threads can continuously extend toward the end of threaded fastener. Those of ordinary skill in the art will appreciate that this can either be done with a single helix, a double helix thread that drops to a single helix, or by using a quadruple helix thread that drops to a double helix thread. The use of a quadruple and double helix thread is found advantageous because it accelerates the rate in which the thread is formed on the shank of the screw during the manufacturing process. It is important, however, that the pair of helices is capable of being intertwined at the leading portion such that when one is terminated at the intermediate portion 2' that the other one can continue to extend to form the continuous second threads 40. Again, at the trailing transition 2A' a similar phenomenon can occur wherein the second thread 40 continues through the trailing transition 2A' where additional cutting flutes 61 are illustrated. At this point, the additional threads can be reintroduced on the shank 20 by having a similar pitch. These additional threads will either be a single helix spirally wrapped about the single helix of the second thread 40 portion to create the third thread 60 or can be a double helix that is positioned between the double helix of a second thread 40 depending on the threading operation used in the manufacture of the screw. These threads then combine to create the third threads 60. As shown in FIGS. 9 and 10 these threads in this third embodiment are the same size. Therefore the screw 10B provides continuous extension of the threaded portion of the fastener creating an initial bone entering cortical screw thread 30 with a self-tapping feature 31 that enables the fastener 10B to then transition to a cancellous bone thread 40 then back to a cortical bone thread 60 thereby when the screw is being fastened and the bone reaches its final attachment location, the exterior cortical bones are securely fastened by the third thread 60 portion. The first threads have a uniform or constant outer diameter between the distal tip and the first leading transition, the first threads have a pitch equal that of the second threads. Alternatively, the second thread can have a pitch half the pitch of the first thread.

Figure 11:
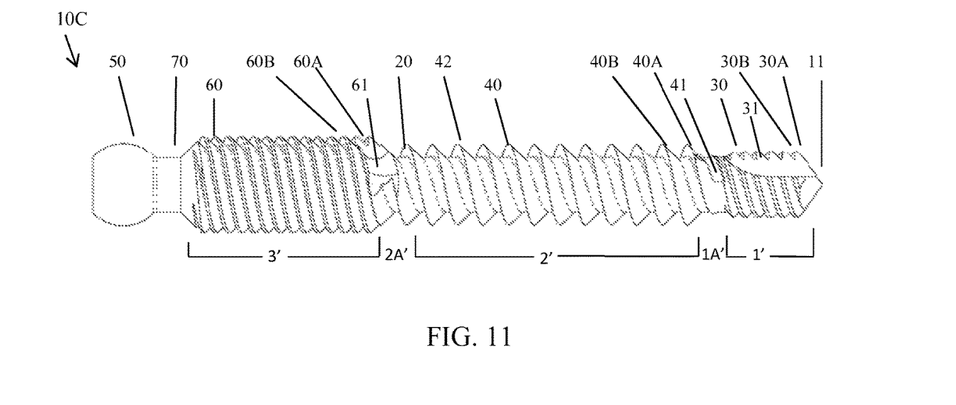
FIG. 11 is a side view of a fourth embodiment of the present invention.
Figure 12:
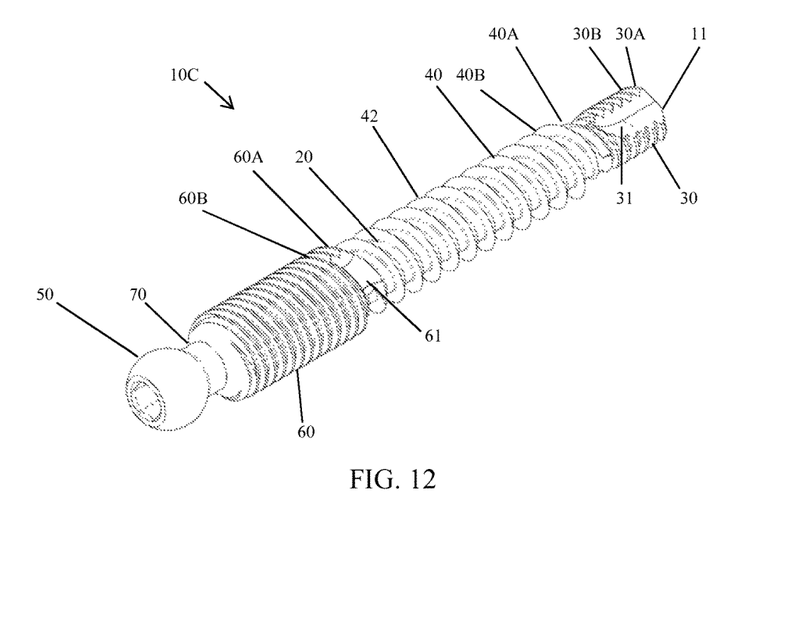
FIG. 12 is a perspective view of the fourth embodiment of FIG. 11.

With reference to FIGS. 11 and 12, a fourth embodiment 10C is shown wherein the third portion and the second portion have a stepped up diameter. In doing this a triple step up diameter occurs where there is an increase in the diameter from the leading portion threads 30 relative to the intermediate portion threads 40 and an additional step up in diameter at the transition between the second threads 40 and the third threads 60.

It is important to note that while these embodiments are shown with various step-ups, it is preferable that the increase in diameter does not exceed several millimeters. In other words, at the leading end, the initial step up can be 1 or 1.5 mm without creating too much of a stress on the bone. As the fastener enters, it can then hit a second transition 2A' increasing an additional 1 to 1.5 mm. Typically, such bone screws are provided in diameters as previously mentioned in the 6.5 to 10 mm range. Smaller diameters can similarly be used in more specialized locations.

Additionally, as shown, each of these embodiments can further have a tulip 80 affixed to the head 50. This is facilitated by the use of a recess 70 and the polyaxial type head 50 as illustrated. All of these features are as previously discussed in the first and second embodiments Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. An orthopedic fastener comprising:
a head;
a shank, the shank extending from the head to a distal tip, the shank having a leading end portion adjacent the distal tip and a trailing end portion adjacent the head and an intermediate portion positioned between the leading and trailing end portions, the intermediate portion has a pair of transitions, a first leading transition at the leading end portion and a second trailing transition at the trailing end portion, at the intermediate portion the shank increasing in diameter to a larger diameter; and
wherein the leading end portion has a first thread extending adjacent the distal tip through to at least the first leading transition, the intermediate portion has a second thread extending from the first leading transition to the second trailing transition, and the intermediate portion has a second thread extending toward the head from the intermediate portion, the second thread of the intermediate portion being larger in outer diameter than the first threads in the leading end portion, the first leading transition having one or more self-tapping cutting grooves extending from at least a first thread in the first leading transition through at least one of said second threads to initiate tapping of the larger second threads into cortical bone, a third portion has a third thread extending from the second trailing transition toward the head, the third thread having one or more cutting grooves extending from at least a second thread in the second trailing transition through at least one of the third threads to initiate tapping of the third thread into cortical bone and wherein the one or more cutting grooves in combination with the threads form threads in the bone to hold the fastener, wherein the leading end portion has one or more cutting grooves adjacent the distal tip and extending from at least a first thread in the leading end portion.

2. The orthopedic fastener of claim 1 wherein the first thread has a pitch equal that of the second thread.

3. The orthopedic fastener of claim 2 wherein the first thread is a double or quadruple helix thread with one or two helix threads extending between the distal end to the head, the first thread increasing in outer diameter at the first leading transition of the second portion to continue as the second thread helix and the other helix terminates at the leading transition.

4. The orthopedic fastener of claim 3 wherein the second thread extends helically spiraled as a single or double helix between the third threads in the trailing end portion, the second thread continues with the third thread to form a double or quadruple helix in the third thread of the third portion.

5. The orthopedic fastener of claim 1 wherein the self-tapping one or more cutting groove allows the larger diameter threads in the intermediate portion to pass through by enlarging or cutting away first threads previously formed at an outer cortical region in the bone to accommodate larger diameter of the second threads to form a larger sized bone thread.

6. The orthopedic fastener of claim 1 wherein a recess is positioned between the head and the trailing end portion.

7. The orthopedic fastener of claim 1 is an implantable metal.

8. The orthopedic fastener of claim 7 wherein the implantable metal is one of titanium, stainless steel or cobalt chrome.

9. The orthopedic fastener of claim 1 further comprises a tulip affixed to the head.

10. The orthopedic fastener of claim 1 wherein the first thread is a double helix, the second thread a single helix and the third thread a double helix.

11. The orthopedic fastener of claim 3 wherein the second thread extends continuously between the distal end to the head, the first thread being part of the second and third thread increasing in one or more helices of outer diameter at the intermediate and trailing transitions.

12. The orthopedic fastener of claim 11 wherein the second thread extends helically spiraled between the third threads in the trailing end portion to form a cortical bone attachment region.

\* \* \* \* \*